United States Patent [19]

Ezer et al.

[11] Patent Number: 4,713,388
[45] Date of Patent: Dec. 15, 1987

[54] CERTAIN 3- OR 4-BENZOYL-2-[(2-AMINOETHYL)THIOPYRIDINES] AND THEIR ANTI-ULCER PROPERTIES

[75] Inventors: Elemer Ezer; Kalman Harsanyi; Hajnalka V. Pethö; Judit Matuz; Laszlo Szporny; Eszter Cholnoky; Csaba Kuthi; Ferenc Trischler; Bela Hegedüs; Marta Kapolnas; Anna Kallay, all of Budapest, Hungary

[73] Assignee: Richter Gedeon Vegyeszeti Gyar Rt., Budapest, Hungary

[21] Appl. No.: 783,875

[22] Filed: Oct. 3, 1985

[30] Foreign Application Priority Data

Oct. 5, 1984 [HU] Hungary ............................. 3775/84

[51] Int. Cl.[4] ................. C07D 213/50; C07D 213/70; A61K 31/44
[52] U.S. Cl. .................................... 514/346; 514/350; 546/291; 546/298
[58] Field of Search ............... 546/291, 298; 514/346, 514/350

[56] References Cited

FOREIGN PATENT DOCUMENTS 552920 8/1981 Japan ................................... 514/350

OTHER PUBLICATIONS

Chem. Abstracts, vol. 96 (5), Abst. No. 96:35096v, Feb. 1, 1982.

*Primary Examiner*—Alan L. Rotman
*Attorney, Agent, or Firm*—Karl F. Ross; Herbert Dubno

[57] ABSTRACT

The invention relates to new 2-pyridine-thiol derivatives of the formula (I),

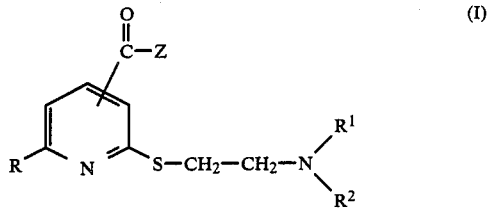

wherein
R is hydrogen or alkyl having from 1 to 4 carbon atoms,
Z is phenyl optionally substituted by one or more halogen atoms and/or alkyl groups having from 1 to 4 carbon atoms,
$R^1$ and $R^2$ each independently represents hydrogen, alkyl having from 1 to 4 carbon atoms, alkylphenyl having from 1 to 4 carbon atoms in the alkyl moiety or an

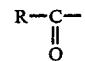

group, in which R has the same meaning as defined above,
and the substituent

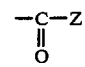

is attached to the pyridine ring in the position 3 or 4, with the proviso that if $R^1$ and $R^2$ are both methyl and Z is 4-chlorophenyl, R is other than hydrogen, and acid addition salts thereof.

The invention further relates to processes for the preparation of the above compounds and to pharmaceutical compositions containing them as active ingredient.

The compounds are pharmaceutically active, in particular show cytoprotective activity.

5 Claims, No Drawings

CERTAIN 3- OR 4-BENZOYL-2-[(2-AMINOETHYL)THIO-PYRIDINES] AND THEIR ANTI-ULCER PROPERTIES

The invention relates to new 2-pyridine-thiol derivatives, More particularly, the invention concerns new 2-pyridine-thiol derivatives of the formula (I)

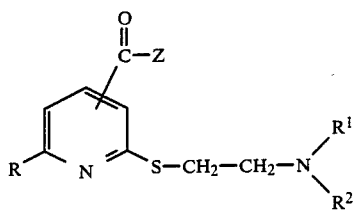

wherein
R is hydrogen or alkyl having from 1 to 4 carbon atoms,
Z is phenyl optionally substituted by one or more halogen atoms and/or alkyl groups having from 1 to 4 carbon atoms,
$R^1$ and $R^2$ each independently represents hydrogen, alkyl having from 1 to 4 carbon atoms, alkylphenyl having from 1 to 4 carbon atoms in the alkyl moiety or an

group, in which R has the same meaning as defined above,
and the

substituent is attached to the pyridine ring in the position 3 or 4,
with the proviso that if $R^1$ and $R^2$ are both methyl and Z is 4-chlorophenyl, R is other than hydrogen, and acid addition salts thereof.

According to another aspect of the invention there is provided a process for the preparation of the new compounds of formula (I) as defined above and acid addition salts thereof, which comprises
(a) reacting a 2-halopyridine derivative of the formula (II),

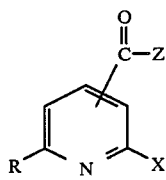

wherein
R and Z are as defined above and
X is halogen,
with a thiol compound of the formula (III),

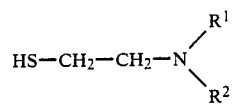

in which $R^1$ and $R^2$ are as defined above, or an acid addition salt thereof; or
(b) reacting a pyridine-2-thione derivative of the formula (IV),

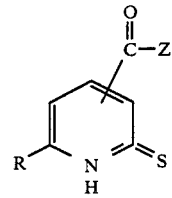

in which R and Z are as defined above, with a 2-haloethyl amine derivative of the formula (V),

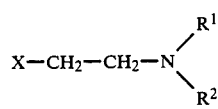

in which $R^1$ and $R^2$ are as defined above and X is halogen, or an acid addition salt thereof; or
(c) reacting a reactive derivative of a 2-hydroxyethylthio pyridine compound of the formula (VI),

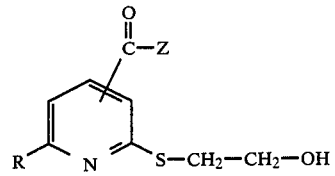

in which R and Z are as defined above, or an acid addition salt thereof, with an amine of the formula (VII),

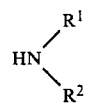

in which $R^1$ and $R^2$ are as defined above; or
(d) to prepare compounds of the formula (I), in which $R^1$ and $R^2$ both represent hydrogen, Z and R are as defined above, reacting a 2-haloethylthio pyridine derivative of the formula (VIII),

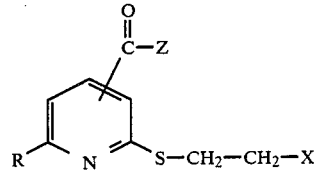

in which
R, Z and X are as defined above, with phthalimide-K, and eliminating the phthaloyl protecting group in a manner known per se, and if desired, in a compound of formulae (I) prepared by any of the processes (a), (b), (c) and (d) converting a group $R^1$ and/or $R^2$ into another group falling under the definition of $R^1$ and $R^2$, respectively, and/or if desired, converting a compound of the formula (I) into an acid addition salt thereof or deliberating same therefrom.

The term "alkyl" as such or as a part of other groups is used in the above definition to refer to straight-chained or branched alkyl groups, e.g. methyl, ethyl, n-propyl, isopropyl, n-butyl, isobutyl, sec.-butyl, tert.-butyl. $R^1$ and $R^2$ as an alkylphenyl group having from 1 to 4 carbon atoms in the alkyl moity preferably represent benzyl.

In the definition of Z the phenyl group preferably is unsubstituted or carries one or two substituents. Particularly preferred phenyl substituents are chlorine and methyl.

The compounds of the formula (I) are pharmaceutically active, in particular show valuable gastrocytoprotective acitivity. According to a still further aspect of the invention there are provided pharmaceutical compositions containing as active agent at least one compound of the formula (I) or a pharmaceutically acceptable acid addition salt thereof, in admixture with pharmaceutical carriers and/or excipients.

Structurally related compounds are disclosed in the Japanese patent application No. 55-2920, published under No. 56-100765, in which the extremely broad formula (I) encompasses also a part of the compounds according to the present invention. There is, however, only a single Example (Example 2) in the above Japanese patent application, illustrating the preparation of a compound, in which the aminoethyl side-chain is attached to the pyridine ring through a thio group: 2-(2-dimethylamino-ethylthio)-3-(4-chlorobenzoyl)-pyridine. All the other specifically disclosed compounds are alkyl- and dialkylaminoalkoxy- or (in a relatively small number) N',N'-dialkylamino-N-alkylamino-pyridine derivatives. Moreover, in the cited patent application the disclosed compounds are mentioned as having anti-apomorphine, muscle relaxant, tranquilizing and cerebral blood flow increasing activities, without any numerical pharmacological data. There is neither hint nor disclosure as to the anti-ulcer, particularly gastrocytoprotective, activity of the compounds.

Of the pyridine compounds certain pyridylacetic acid thioamides have so far been reported as useful in the therapy of gastrointestinal ulceration. More particularly, tiquinamide.HCl (Wy-24081) having gastric acid secretion inhibiting activity, the anti-gastrine α-phenyl-2-pyridine-ethane-thioamide (Sc-15395) and α-methoxy-N-methyl-2-pyridine ethane thioamide (SKF-59377) are known in the art. In a recent publication (J. Med. Chem. 26, 538 1983) the gastric acid secretion inhibiting properties of 2-pyridyl-urea derivatives have been described. All these compounds are structurally substantially different from the new compounds according to the invention.

In addition to the traditional anti-acid preparations the so-called cytoprotective compounds have recently attracted a world-wide attention. The term "cytoprotection" has been defined by A. Robert (Gastroenterology, 77: 761-767 (1979)) in connection with prostaglandines, but the mechanism of cytoprotection is not entirely clear up to date. According to Robert in the cytoprotective effect prostaglandins have a leading part, while it has recently been proved that also the so-called sulfhydryls have an important role (Szabó et al.: Science, 214, 200-2 (1981)).

We have surprisingly found that the new 2-pyridine-thiol derivatives of the formula (I), which have no structural relationship with prostaglandins, are very potent in the treatment of experimentally induced ulceration. In lower doses they show cytoprotective activity, while in 100 to 500 times higher doses descrease the gastric acid secretion as well.

The pharmacological activity of the new compounds has been investigated by the following methods:

Gastric necrosis induced by acidic ethanol
(cytoprotective activity)

Female RG-Wistar rats weighing 120 to 150 g. each were fasted for 24 hours. Water was given ad libitum. The compounds to be tested were administered orally, 30 minutes prior to the oral administratio of a mixture of 1 ml. of concentrated hydrochloric acid and 50 ml. of absolute ethanol in a dose of 0.5 ml./100 g. of body weight. One hour later the animals were killed by overdosing with ether, Stomachs were removed and opened along the major curvature. After cleaning the wet weight of the stomachs was determined, and the difference between the wet weight obtained and the wet weight of the stomachs of untreated (control) animals was calculated, in order to determine the degree of gastric oedema. The stomachs were then dried and the gastric lesions were observed visually. Lengths of lesions were measured in millimeters (Derelanko and Long, Proc. Soc. Exp. Biol. and Med. 166, 394 (1981)), and the length of the average lesions per stomach was given. Degree of cytoprotection was expressed in % related to the control.

The statistical evaluation of the results was carried out by the Student test.

The results of the above test for a particularly preferred compound according to the invention ("A") are summarized in Table 1, while Table 2 shows the $ED_{50}$-values of certain compounds of formula (I). Test compounds:

A=2-[(2-aminoethyl)-thio]-3-benzoyl-pyridine.HCl
B=3-benzoyl-2-{[2-(N,N-diacetylamino)-ethyl]-thio}-pyridine
C=2-[(2-aminoethyl)-thio]-3-(p-chlorobenzoyl)-pyridine.HCl
D=2-[(2-aminoethyl)-thio]-3-(2,5-dimethylbenzoyl)-pyridine.HCl
E=2-[(2-aminoethyl)-thio]-4-benzoyl-6-propyl-pyridine.2HCl

TABLE 1

| | Gastric necrosis induced by acidic methanol | | | | | |
|---|---|---|---|---|---|---|
| Pre-treatment | N | Dose (mg./kg.) p.o. | Oedema (mg.) | Inhibition (%) | Haemorrhagic injury (mm) | Inhibition (%) |
| acidic-methanolic control | 25 | — | 379 ± 43 | — | 85 ± 15 | — |
| A | 8 | 0.05 | 307 ± 42 | 19 | 48 ± 19 | 45 |
| A | 10 | 0.1 | 209 ± 51 | $45^x$ | 38 ± 18 | $56^x$ |
| A | 12 | 1.0 | 72 ± 28 | $82^{xx}$ | 5 ± 1.5 | $96^{xx}$ |
| A | 12 | 10.0 | 22 ± 12 | $95^{xx}$ | 6 ± 3 | $94^{xx}$ |
| cimetidine | 8 | 25 | 441 ± 82 | — | 82 ± 21 | 2 |
| cimetidine | 8 | 100 | 301 ± 42 | 21 | 42 ± 13 | 46 |

$^x p < 0.05$ related to the control group treated with
$^{xx} p < 0.01$ acidic methanol

TABLE 2

The ED$_{50}$-value of certain compounds in the acidic methanol

| Test compound | Gastric oedema inhibition ED$_{50}$(mg/kg. p.o.) | Haemorrhagic injury inhibition ED$_{50}$(mg./kg. p.o.) |
| --- | --- | --- |
| A | 0.2 | 0.1 |
| B | 1.0 | 2.0 |
| C | 10.0 | 15.0 |
| D | 10.0 | 10.0 |
| E | 20.0 | 25.0 |

Gastric acid secretion inhibiting activity on Shay rats (Gastroenterology, 5, 43–46 (1945))

Femal H-Wistar rats weighing 120–150 g each were fasted for 24 hours. Water was added ad libitum. The pylorus of the animals was ligated under light ether narcosis. The test drugs were administered during the operation, partially orally, partially intraperitoneally. 4 hours after treatment the animals were killed by an overdose of ether. The stomach was excised and cut along the large curvature. The volume and the pH of the contents were determined and in each case the HCl production was determined by titration.

The results obtained are shown in Table 3.

TABLE 3

Gastric acid secretion inhibiting activity on Shay rats (oral and intraperitoneal treatment)

| Treatment | N | Dose (mg./kg.) | Secretion HCl/4 hours μmol/100 g body weight | Secretion HCl inhibition (%) |
| --- | --- | --- | --- | --- |
| Control | 10 | — | 564 ± 42 | — |
| A | 5 | 5 p.o. | 357 ± 35 | 37 |
| A | 15 | 10 p.o. | 350 ± 38 | 38 |
| A | 15 | 20 p.o. | 372 ± 40 | 34 |
| A | 5 | 40 p.o. | 124 ± 27 | 70$^x$ |
| A | 5 | 6 i.p. | 505 ± 29 | 11 |
| A | 10 | 12 i.p. | 200 ± 30 | 65$^x$ |
| A | 5 | 25 i.p. | 0 | 100 |

$^x$p < 0.01 related to the control group ED$_{50}$:50 mg./kg.

Indomethacin-induced antral and intestinal ulceration

Female RG-Wistar rats weighing 120 to 150 g. each were fasted for 24 hours. Water was added ad libitum. The animals were then given access to food for one hour, and 30 minutes after the administration of the test compounds a 15-mg./kg. oral dose of indomethacin was administered. 24 hours after indomethacin-treatment the animals were killed by overdose of ether. Stomachs and the entire intestine were removed, the stomachs were opened along the main curvature, and the total ulcerated area (ulceration index, mm$^2$) was determined.

To evaluate the development of intestinal ulcers the so-called inflation technique of Ezer and Szporny (J. Pharm. Pharmacol. 27, 866 (1975)) was employed. The tensile strength of the intestinal wall expressed in mmHg weakens gradually parallel with the progress of ulceration. The statistical evaluation was carried out by the Student test. The results obtained are set forth in Table 4.

TABLE 4

Inhibition of indomethacin-induced ulceration

| | | | Intestinal ulcer | Antral ulcer | |
| --- | --- | --- | --- | --- | --- |
| Treatment | N | Dose (mg./kg. p.o.) | t.s. 24 hours after indomethacin treatment (mmHg) | Ulceration index (mm$^2$/stomach) | Rats having no ulcer |
| Indomethacin — control | 50 | 15 + carrier | 147 ± 11 | 14.8 | 15 |
| Indomethacin + A | 15 | 15 + 5 | 162 ± 14 | 18.9 | 3 |
| Indomethacin + A | 20 | 15 + 25 | 198 ± 9$^x$ | 4.0$^x$ | 12$^x$ |
| Indomethacin + Pirenzepine | 20 | 15 + 25 | 152 ± 18 | 12.0 | 5 |
| Indomethacin + Cimetidine | 10 | 15 + 50 | 161 ± 8 | 14.7 | 2 |

$^x$p <0.01 related to the control treated with indomethacin
t.s.: tensile strength Inhibition of aspirin-induced gastric ulceration Female H. Wistar rats weighing 120 to 150 g each were fasted for 24 hours. Water was given ad libitum. The stomach ulcer was induced by oral administration of aspirin in a dose of 100 mg./kg. (in Tween 80 suspension). The test drug was given simultaneously with the administration of aspirin, orally. The animals were killed by overdose of ether, 4 hours after treatment. The stomach was excised and cut along the large curvature. The red-brownish erosions on the glandular surface were counted. When evaluating the test results, the number of ulcers per stomach and its proportion to the number of ulcers found in the stomachs of control animals (inhibition of ulceration) were determined. The results are shown in Table 5.

TABLE 5

Inhibition of aspirin-induced gastric ulceration

| Treatment | N | Dose (mg./kg. p.o.) | Ulcer/stomach | Inhibition (%) |
| --- | --- | --- | --- | --- |
| Aspirin — control | 30 | 100 + carrier | 15.0 + 3.1 | — |
| Aspirin + A | 20 | 100 + 1 | 9.4 + 4.1 | 38 |
| Aspirin + A | 10 | 100 + 2 | 8.0 + 3.0 | 47$^x$ |
| Aspirin + A | 10 | 100 + 10 | 3.7 + 4.5 | 76$^x$ |

$^x$ED$_{50}$ 2.1 mg./kg.

From the test results obtained it can be concluded that the compounds according to the invention have gastrocytoprotective properties. For example in case of Compound A the gastric acid secretion inhibiting activity was observed only in an about 500-times higher dose, accordingly, the compound has a selective gastrocytoprotective activity. This activity is not eliminated by indomethacin pre-treatment, therefore, should be a process independent from prostaglandins.

As mentioned hereinbefore, the compounds of the formula (I), in which R, Z, R$^1$ and R$^2$ are as defined above, may be prepared by the processes (a) to (c).

According to process (a) the reaction of the compounds of formula (II) with the compounds of formula (III) is performed in a solvent, preferably in the presence of an acid binding agent. As a solvent preferably lower alcohols having from 1 to 4 carbon atoms, water or a mixture thereof may be employed. Preferred acid binding agents are the alkali metal hydroxides, carbonates, alcoholates or organic bases, such as triethyl amine or quaternary ammonium compounds. The reaction temperature may vary within a wide range, depending on the solvent employed and on possible side-reactions. It is preferred, however, to carry out the reaction between 25° C. and 80° C. in order to achieve an acceptable reaction rate. By proper selection of the solvent it can be ensured that after termination of the reaction the inorganic salts may be filtered off. After evaporation of the reaction mixture the crystalline products may be purified by recrystallization, and the products, which cannot be crystallized in base form can be isolated from their aqueous solutions by extraction with water-immiscible organic solvents, such as chlorinated hydrocarbons, ethers or ethyl acetate, and evaporation of the organic phase. If desired, the product can further be purified by distillation in vacuum. The products having poor crystallization properties in a base form can be converted into corresponding, readily crystallizable acid addition salts, preferably hydrochlorides.

The process (a) according to the invention can be accomplished in an acidic medium, too. In this case the reactants are reacted preferably in a concentrated aqueous hydrochloric acid solution, at the boiling point of the reaction mixture.

In process (b) the reaction is carried out essentially as described in connection with process (a), first variant, in the presence of a base.

In process (c) as a reactive derivative of the compounds of the formula (VI) preferably their halides are employed. The reactive derivatives of the compounds of formula (VI) or the acid addition salts thereof are reacted with an excess amount of an amine of the formula (VII) in an organic solvent, optionally under pressure. Of the compounds of formula (VII) preferably an excess of 2–5 moles is employed, and the reaction temperature is generally between 50° C. and 150° C. As a solvent preferably alcohols, chlorinated organic solvents or solvents of acid amide type, e.g. dimethyl formamide, can be used.

Process (d) by which primary amines can be prepared ($R^1$ and $R^2$ both stand for hydrogen), is carried out under the reaction conditions of Gabriel synthesis, in an inert organic solvent, preferably dimethyl formamide, preferably at a slightly elevated temperature. The phthaloyl protecting group is preferably eliminated by hydrolysis in the presence of a base, which may for example be hydrazine or methyl amine.

Compounds of the formula (II) are known in the art (see European patent application No. 8010027.2, published under No. 0032516), or can easily be prepared by known chemical reactions (Org. Synth. Coll. Vol. 4, 88 (1963)); Wolfenstain and Hartwich, Ber. 48, 2043 (1915)).

Compound of formula (III) in process (a), compounds of formula (V) in process (b) and compounds of the formula (VII) in process (c) (wherein the substituents are as hereinabove defined) and phthalimide-K are known, commercially available substances, or can easily be prepared from such compounds, by methods known in the art.

Compounds of formula (IV) are partly known, partly can be prepared from known compounds in a manner known per se.

The new compounds of the formula (VI) and their reactive derivatives, e.g. the halides of the formula (VIII) can be prepared according to our co-pending Hungarian patent application No. 3777/84. Chlorides may, for example, be prepared from 3-benzoyl-2-(2-hydroxyethyl)thiopyridine by chlorinating agents suitable for replacing the hydroxyl group, e.g. thionyl chloride. The reaction may for example be performed by starting from an acid addition salt of the hydroxyethyl compound, in an organic solvent, e.g. chloroform, benzene, acetonitrile; or a dipolar aprotic solvent. Further, reactive esters can be prepared from the above starting material with sulfonic acid chlorides, e.g. p-toluenesulfonic acid chloride or methane-sulfonic acid chloride, or they can be converted into acid addition salts, e.g. hydrochlorides.

As mentioned before, in the new compounds of the formula (I) the substituents $R^1$ and/or $R^2$ can be converted into other substituents falling under the definition of $R^1$ and $R^2$, respectively.

For example the compounds of the formula (I), in which $R^1$ and $R^2$ both stand for hydrogen, may be converted into the corresponding compounds, in which $R^1$ and/or $R^2$ represents an

group (R is as defined above) by acylation.

From the acyl compounds ($R^1$ and/or $R^2$ stands for an

group, in which R is as defined above) in turn, the acyl group can be eliminated by hydrolysis, in a known manner to yield the corresponding primary amines.

By the reductive condensation of the primary amines of the formula (I), in which $R^1$ and $R^2$ both stand for hydrogen, and aldehydes or ketones secondary or, in a second step, by adding further reactants, tertiary amines can be prepared ($R^1$ and/or $R^2$ is a $C_{1-4}$-alkyl or $C_{1-4}$-alkyl-phenyl group). For example by condensing an aldehyde or ketone of the formula (IX)

with a primary amine of the formula (I) in the presence of a reducing agent secondary or tertiary amines containing the corresponding $R^1$ and $R^2$ groups are obtained. As a reducing agent preferably formic acid or a derivative thereof or e.g. sodium borohydride is employed. This method is particularly convenient for the preparation of compounds of the formula (I), in which $R^1$ and/or $R^2$ stands for a $C_{1-4}$-alkyl or $C_{1-4}$-alkyl-phenyl group, preferably a methyl or benzyl group.

Compounds of the formula (I) can be converted into their acid addition salts by reaction with suitable acids. For this purpose pharmaceutically acceptable acids are preferred.

Salt formation can be carried out, for example, in an inert organic solvent such as a $C_{1-6}$-aliphatic alcohol in such a way that the compound of the formula (I) is dissolved in the solvent and the selected acid or a solution thereof formed with the same solvent is added to the firt solution until it becomes slightly acidic. Thereafter the acid addition salt separates and can be removed from the reaction mixture e.g. by filtration.

The active compounds of the formula (I) may be formulated for therapeutic purposes. The invention therefore relates also to pharmaceutical compositions comprising as active ingredient at least one compound of formula (I),in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, etc. can be used. The compounds can be formulated as conventional pharmaceutical formulations, for example in a solid (globular and angular pills, dragées, capsules, e.g hard gelatine capsules) or liquid (injectable oily or aqueous solutions or suspensions) form. The quantity of the solid carrier can be varied within wide ranges, but preferably is between 25 mg. and 1 g. The compositions optionally contain also conventional pharmaceutical additives, such as preserving agens, wetting agents, salts for adjusting the osmotic pressure, buffers, flavoring and odoring substances. The pharmaceutical compositions may be peepared by conventional techniques including sieving, mixing, granulation and pressing. The formulations obtained may then be subjected to additional conventional treatments, such as sterilization.

The invention is elucidated in detail by the aid of the following non-limiting examples.

According to the Chemical Abstracts nomenclature the compounds of formula (I) are substituted methanones or acid amides, depending on the characteristic functional group. For sake of convenience in the Examples the compounds are designated as substituted pyridines (on the basis of the pyridine ring present in all of the compounds), but the designation according to the Chemical Abstracts nomenclature is also given.

EXAMPLE 1

2-[(2-Aminoethyl)-thio]-3-benzoyl-pyridine.HCl
{2-[(2-Aminoethyl)-thio]-3-pyridinyl}-phenyl-methanone.HCl (a) To a hot solution of 10.88 g. (0.05 moles) of 3-benzoyl-2-chloropyridine and 8.51 g.) 0.075 moles) of cysteamine.HCl in 100.0 cm$^3$ of ethanol a solution of 9.88 g. (0.15 moles) of 85% potassium hydroxide in 50.0 cm$^3$ of ethanol is added dropwise, in 30 minutes. The reaction is boiled for further 30 minutes, neutralized with concentrated hydrochloric acid, the inorganic salt is filtered off and the solution is evaporated. The residue is dissolved in water, extracted with 1,2-dichloroethane at pH 4 and subsequently at pH 11, and the extract obtained is washed with water and evaporated. The oily evaporation residue is converted into the corresponding hydrochloride with a solution of hydrochloric acid in ethanol, and the salt obtained is recrystallized from ethanol. 9.90 g. (67.2%) of 2-[(2-aminoethyl)-thio]-3-benzoylpyridine.HCl are obtained, melting at 190° to 192° C.

(b) Carrying out the reaction between 3-benzoyl-2-chloropyridine and cysteamine.HCl in a concentrated aqueous hydrochloric acid solution, again 2-[(2-aminoethyl)-thio]-3-benzoyl-pyridine.HCl is obtained, melting at 190° to 191° C.

(c) 1.60 g. (0.04 moles) of sodium hydroxide are dissolved in 25.0 cm$^3$ of water. 4.31 g. (0.02 moles) of 3-benzoyl-1,2-dihydropyridine-2-thione and 2.32 g. (0.02 moles) of 2-chloroethylamine.HCl are then added to the solution, and the reaction mixture is boiled for 40 minutes. After cooling, the mixture is extracted with 1,2-dichloroethane at pH 4 and then pH 11, whereupon the latter dichloroethane phase is extracted with an aqueous hydrochloric acid solution. The aqueous phase is evaporated and the crystalline crude product is recrystallized from ethanol. The 2-[(2-aminoethyl)-thio]-3-benzoyl-pyridine.HCl obtained melts at 190° to 191° C.

Analysis for C$_{14}$H$_{14}$N$_2$OS.HCl (294,80) Calculated: C 57.04%, H 5.13%, Cl 12.02%, N 9.50%, S 10.88%; found: C 56.94%, H 5.22%, Cl 11.57%, N 9.67%, S 10.72%.

IR spectrum (KBr) 1648 cm$^{-1}$ >C=O, 1284 cm$^{-1}$ —S—CH$_2$—, 1598, 788, 701 cm$^{-1}$ —Ar, 3200–2300 cm$^{-1}$

NMR spectrum (DMSO d$_6$) 3.13 ppm m —S—CH$_2$—, 3.37 ppm m —N—CH$_2$—, 7.1 ppm 2xd pyridine 4,5-H, 7.2–7.7 ppm m phenyl ring, 8.11 ppm b, 8.4 ppm 2xd pyridine 6-H.

EXAMPLE 2

3-Benzoyl-2-{[2-(N,N-diacetylamino)-ethyl]-thio}-pyridine

N-Acetyl-N-{2-[(3-benzoyl-2-pyridinyl)-thio]-ethyl}-acetamide 16.54 g. (0.056 moles) of 2-[(-aminoethyl)-thio]-3-benzoyl-pyridine HCl are dissolved in water. The solution is rendered alkaline, the base is extracted with ethyl acetate and evaporated. To the residue 50 cm$^3$ (54.1 g., 0.53 moles) of acetic acid anhydride are added, and the reaction mixture is boiled for 30 minutes. The excess of anhydride is then decomposed with 50 cm$^3$ of water and the solution is evaporated. The crystalline residue is triturated with ether, filtered and recrystallized from ethanol. The obtained 2-benzoyl-2-{[2-(N,N-diacetylamino)-ethyl]-thio}-pyridine melts at 104° to 105° C.

Analysis for C$_{18}$H$_{18}$O$_3$NS (342.41): Calculated: C 63.14%, H 5.30%, N 8.18%, S 9.36%; found: C 63.21%, H 5.56%, N 8.16%, S 9.21%.

IR spectrum (KBr): 1704, 1692 cm$^{-1}$ >C=O amide, 1642 cm$^{-1}$ >C=O ketone, 1598, 787, 753, 708 cm$^{-1}$ —Ar.

NMR spectrum (CDCl$_3$): 2.5 ppm S —Ac—CH$_3$, 3.4 ppm m —S—CH$_2$—, 4.0 ppm m —N—CH$_2$—, 7.2 ppm 2xd pyridine 4,5-H, 7.6 ppm m phenyl ring, 8.7 ppm m pyridine 6-H.

EXAMPLE 3

2-[(2-Aminoethyl)-thio]-3-(p-chlorobenzoyl)-pyridine.HCl

2-{[(Aminoethyl)-thio]-3-pyridinyl}-4-chlorophenyl-methanone.HCl

To a solution of 16.2 g. (0.05 moles) of 2-chloro-3-(p-chlorobenzoyl)-pyridine and 8.52 g. (0.075 moles) of cysteamine.HCl in 30 cm$^3$ of ethanol a solution of 9.9 g. (0.15 moles) of 85% potassium hydroxide in 35 cm$^3$ of ethanol is added dropwise at room temperature, within 30 minutes. The suspension is stirred for 23 hours and neutralized with a concentrated aqueous hydrochloric acid solution. The inorganic salt is filtered off, and the ethanolic solution is evaporated. The solid residue is dissolved in water, alkalized up to pH 10 and extracted with ethyl acetate. The ethyl acetate phase is evaporated the residual oily base is converted into its hydrochloride with hydrochloric acid in isopropanol, which is then filtered, dried and recrystallized from nitromethane. 2-[(2-aminoethyl)-thio]-3-(p-chlorobenzoyl)-pyridine.HCl is obtained, melting at 171° to 173° C.

Analysis for C$_{14}$H$_{13}$ClN$_2$OS.HCl (329.24): Calculated: C 51.07%, H 4.29%, N 8.51%, S 9.74%; found: C 50.94%, H 4.17%, N 8.70%, S 9.46%.

IR spectrum (KBr): 3250–2300 cm$^{-1}$ —N$^+$H, 1655 cm$^{-1}$ >C=O, 1088 cm$^{-1}$ —Ar—Cl, 1590, 842, 815, 765 cm$^{-1}$ —Ar.

NMR spectrum (CDCl$_3$+DMSO d$_6$) 3.4 ppm m —S—CH$_2$— and —N—CH$_2$—, 7.5 ppm m pyridine 4,5-H and phenyl ring, 8.7 ppm 2xd pyridine 6-H.

EXAMPLE 4

2-[(2-Aminoethyl)-thio]-3-(2,5-dimethylbenzoyl)-pyridine.HCl

{2-[(2-Aminoethyl)-thio]-3-pyrdinyl}-2,5-dimethylphenyl-methanone.HCl

To a hot solution of 24.6 g. (0.1 mole) of 3-(2,5-dimethylbenzoyl)-2-chloro-pyridine and 17.04 g. (0.15 moles) of cysteamine.HCl in 200 cm$^3$ of ethanol a solution of 19.3 g. (0.3 moles) of 85% aqueous potassium hydroxide in 100 cm$^3$ of ethanol is added dropwise, in 30 minutes. The mixture is boiled for additional 20 minutes and is diluted with 450 cm$^3$ of water. The pH of the solution is adjusted to 2 and it is extracted with diisopropyl ether. Thereafter the pH is adjusted to 11 and the mixture is extracted with ethyl acetate. The ethyl acetate phase is evaporated, from the oily residue salt is prepared with hydrochloric acid in isopropanol, which is then filtered off and recrystallized from isopropanol. 16.07 g. (49.7% of 2-[(2-aminoethyl)-thio]-3-(2,5-dimethylbenzoyl)pyridine.HCl are obtained, melting at 208° to 210° C.

Analysis for C$_{16}$H$_{18}$N$_2$SO.HCl (322.85): Calculated: C 59.53%, H 5.93%, N 8.68%, S 9.93%; found: C 59.70%, H 6.10%, N 8.74%, S 9.77%.

IR spectrum (KBr): 1660 cm$^{-1}$ >C=O, 3250–2400 cm$^{-1}$ —N$^+$H, 1580, 810, 770 cm$^{-1}$ —Ar.

NMR spectrum (CDCl$_3$): 2.3 ppm s —Ar—CH$_3$, 3.6 ppm s —S—CH$_2$— and —N—CH$_2$—, 7.3 ppm m pyridine 4.5-H and phenyl 3,4,6-H, 7.8 ppm 2xd pyridine 6-H, 8.9 ppm x$_b$

EXAMPLE 5

2-[(2-Aminoethyl)-thio]-4-benzoyl-6-propyl-pyridine.2HCl

{2-[(2-Aminoethyl)-thio]-6-propyl-4-pyridinyl}-phenyl-methanone.2HCl

To a hot solution of 23.37 g. (0.09 moles) of 4-benzoyl-2-chloro-6-propyl-pyridine and 20.43 g. (0.18 moles) of cysteamine.HCl in 60 cm$^3$ of ethanol a solution of 22.4 g. (0.34 moles) of 85% potassium hydroxide in 90 cm$^3$ of ethanol are added. The suspension obtained is boiled for 4.5 hours and is then diluted with 500 cm$^3$ of water. The solution is acidified with concentrated hydrochloric acid to pH 1, extracted with diisopropyl ether, the pH of the aqueous phase is adjusted to 10, and it is extracted with ethyl acetate. The ethyl acetate phase is evaporated, the residual oily base is converted into the corresponding hydrochloride with hydrochloric acid in ethyl acetate, and the salt is recrystallized from n-buthanol. 2-[(2-aminoethyl)-thio]-4-benzoyl-6-propyl-pyridine.2HCl is obtained, melting at 185° C.

Analysis for C$_{17}$H$_{20}$N$_2$OS.2HCl (373.33): Calculated: C 54.69%, H 5.94%, N 7.50%, Cl 18.99%; found: C 54.65%, H 5.78%, N 7.58%, Cl 18.58%.

IR spectrum (KBr): 3200–2100 cm$^{-1}$

1664 cm$^{-1}$ >C=O, 1286 cm$^{-1}$ —S—CH$_2$—, 1598, 802, 721, 692 cm$^{-1}$ —Ar,

NMR spectrum (D$_2$O) 1.3 ppm t Pr—CH$_3$, 2.0 ppm q CH$_2$—CH$_2$—CH$_3$, 3.2 ppm t Ar—CH$_2$—R, 3.9 ppm m —S—CH$_2$— and

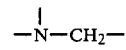

8.0 ppm m Ar—H,

EXAMPLE 6

2-[(2-N,N-Dimethylaminoethyl)-thio]-3-benzoyl-pyridine.HCl

2-{[(2-N,N-Dimethylaminoethyl)-thio]-3-pyridinyl}-phenylmethanone.HCl 14.75 g. (0.05 moles) of 2-[(2-aminoethyl)-thio]-3-benzoyl-pyridine.HCl are dissolved in water. The solution is alkalized and shaken with ethyl acetate. The ethyl acetate extracts are evaporated, to the residue 13.5 g. of 85% formic acid and subsequently 9.4 g. of 35% formaline are added and the mixture is boiled for 20 hours. Thereafter 4.3 cm$^3$ of concentrated hydrochloric acid are added to the mixture, which is then evaporated. The residue is dissolved in water, alkalized, shaken with ethyl acetate and dried. The corresponding hydrochloride is precipitated by introducing hydrogen chloride gas into the mixture. 2-[(2-N,N-Dimethylaminoethyl)- thio]-3-benzoyl-pyridine.HCl is obtained, melting at 146° to 148° C.

Analysis for $C_{16}H_{19}ClN_2OS$ (322.86): Calculated: C 59.52%, H 5.93%, Cl 10.98%, N 8.68%, S 9.93%; found: C 59.58%, H 5.85%, Cl 11.11%, N 8.75%, S 9.69%.

IR spectrum (KBr) 2800–2000 $cm^{-1}$

2810 $cm^{-1}$ >N—CH$_3$, 1650 $cm^{-1}$ >C=O, 1280 $cm^{-1}$ —S—CH$_2$—, 1588, 800, 760, 712 $cm^{-1}$ —Ar.

NMR spectrum (D$_2$O) 3.3 ppm s >N—CH$_3$, 3.7 ppm s —S—CH$_2$+N—CH$_2$, 7.8–7.9 ppm m phenyl ring-+pyridine 4,5-H, 8.9 ppm 2xd pyridine 6-H.

EXAMPLE 7

N-(1-Phenyl-2-propyl)-2-[(2-aminoethyl)-thio]-3-benzoylpyridine 1.32 g. (0.02 moles) of 85% potassium hydroxide are dissolved in 8 cm$^3$ of methanol, and the solution obtained is added to the solution of 5.9 g. (0.02 moles) of 2-[(2-aminoethyl)-thio]-3-benzoyl-pyridine hydrochloride and 2.64 cm$^3$ of benzylmethyl ketone in 20 cm$^3$ of methanol. Thereafter 0.k9 g (0.0005 moles) of sodium borohydride are added portionwise to the mixture at 40° C., within one hour. The reaction mixture is stirred for further 10 hours, evaporated, extracted with chloroform, evaporated again and treated with ether. The weight of the product dissolved in ether in 3.41 g., and the product becomes crystalline uner nitromethane. After recrystallization from acetonitrile 0.7 g. of the title compound are obtained, melting at 92° C.

Analysis for $C_{23}H_{26}N_2OS$ (378.53): calculated: C 72.97%, H 6.92%, N 7.40%, S 8.47%; found: C 72.90%, H 7.00%, N 7.25%, S 8.90%.

IR spectrum: (KBr): 3300–220 $cm^{-1}$ OH+NH, 1082 $cm^{-1}$ C—OH, 1591, 1570 $cm^{-1}$ Ar skeleton, 783, 748, 700 $cm^{-1}$ Ar H def.

NMR spectrum (CDCl$_3$): 1.1 ppm d —CH$_3$, 2.5–3.4 ppm m Ar—CH$_2$, S—CH$_2$, N—CH$_2$, N—CH, 6.0 ppm s O—CH, 6.8–8.3 ppm m Ar—H.

We claim:

1. A compound of the Formula (I)

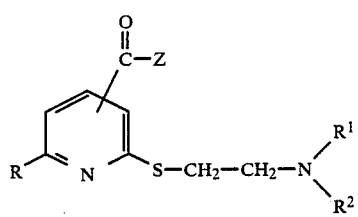

wherein
R is hydrogen or C$_1$ to C$_4$ alkyl;
Z is phenyl, 4-chloro-phenyl, or 2,5-dimethyl-phenyl;
R$^1$ and R$^2$ are each an

group; and
the

substituent is bonded to the 3- or 4-position of the pyridine ring; or a pharmaceutically acceptale acid addition salt thereof.

2. 3-Benzoyl-2-[2-(N,N-diacetylamino)-ethyl]-thiopyridine.

3. A gastrocytoprotective method of preventing ulcers which comprises the step of administering to a mammalian subject susceptible to gastric ulceration, a therapeutically effective amount of a compound of the Formula (I)

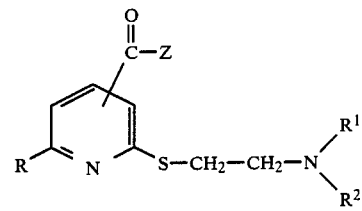

wherein
R is hydrogen or C$_1$ to C$_4$ alkyl;
Z is phenyl, 4-chloro-phenyl, or 2,5-dimethyl-phenyl;
R$^1$ and R$^2$ are each hydrogen, C$_1$ to C$_4$ alkyl, C$_1$ to C$_4$ alkyl phenyl, or an

group; and
the

substituent is bonded to the 3- or 4-position of the pyridine ring; or a pharmaceutically acceptable acid addition salt thereof.

4. A cytoprotective pharmaceutical composition which comprises as active ingredient a therapeutically effective amount of a compound of the Formula (I) as defined in claim 1 or a pharmaceutically acceptable acid addition salt thereof.

5. A gastrocytoprotective method of treating ulcers which comprises the step of administering to a mammalian subject susceptible to gastric ulceration, a therapeutically effective amount of the compound of the Formula (I) as defined in claim 1 or a pharmaceutically acceptable acid addition salt thereof.

* * * * *